United States Patent [19]

Uetake et al.

[11] Patent Number: 4,736,842
[45] Date of Patent: Apr. 12, 1988

[54] PROTECTOR FOR SURGICAL KNIFE

[76] Inventors: Tsuyoshi Uetake; Iwao Ueno, both of 19-6, Hongo 3-chome, bunkyou-ku, Tokyo, Japan

[21] Appl. No.: 22,419

[22] Filed: Mar. 6, 1987

[30] Foreign Application Priority Data

Aug. 15, 1986 [JP] Japan .................. 61-125365[U]

[51] Int. Cl.$^4$ .................................................. B65D 81/02
[52] U.S. Cl. ........................................ 206/363; 206/349; 30/164
[58] Field of Search ............. 206/363, 349, 352; 30/164

[56] References Cited

U.S. PATENT DOCUMENTS 4,050,576  9/1977  Williams et al. ............... 206/363
4,180,162 12/1979  Magney ............................ 206/363
4,344,532  8/1982  Eldridge, Jr. et al. ......... 206/363
4,385,692  5/1983  Eldridge, Jr. .................... 206/363
4,511,035  4/1985  Alpern ............................... 206/363

Primary Examiner—Joseph Man-Fu Moy
Attorney, Agent, or Firm—James W. Hellwege

[57] ABSTRACT

A protector for a surgical knife having an edge portion and a stem portion is disclosed. The protector is formed by a mold of synthetic resin and comprises a base plate having a peripheral shape substantially corresponding to a peripheral configuration of the edge portion of the knife, an upright ridge formed along a periphery of the base plate except for a portion through which the stem portion of the knife fit in the protector extends, and at least one projection formed on the base plate at a position at which a hole formed in the stem portion of the knife situates upon fitting the knife in the protector.

9 Claims, 3 Drawing Sheets

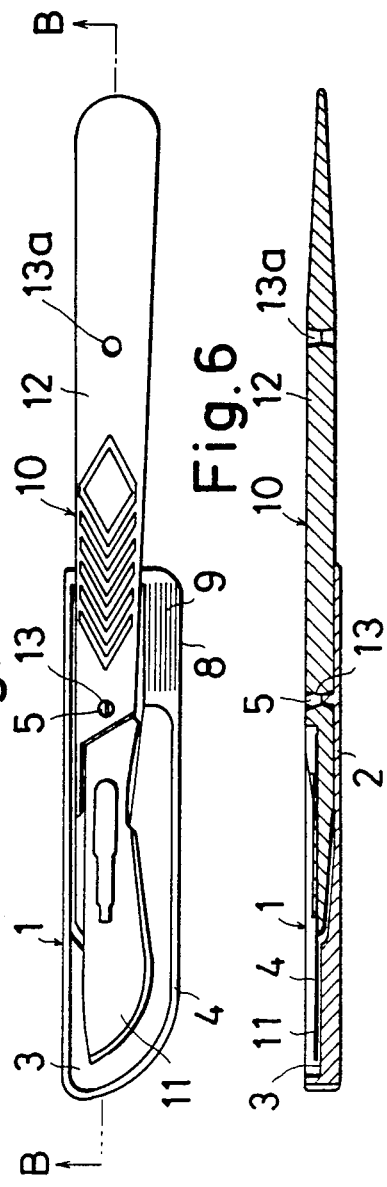

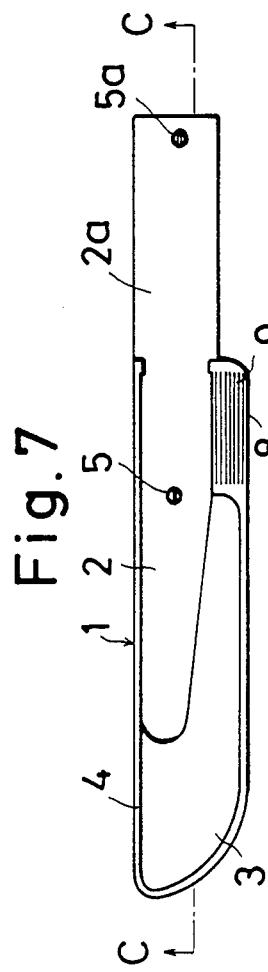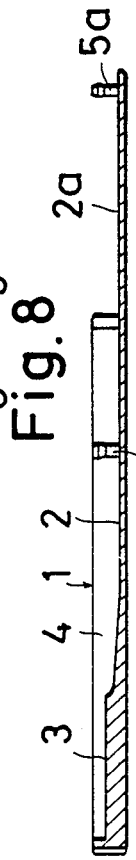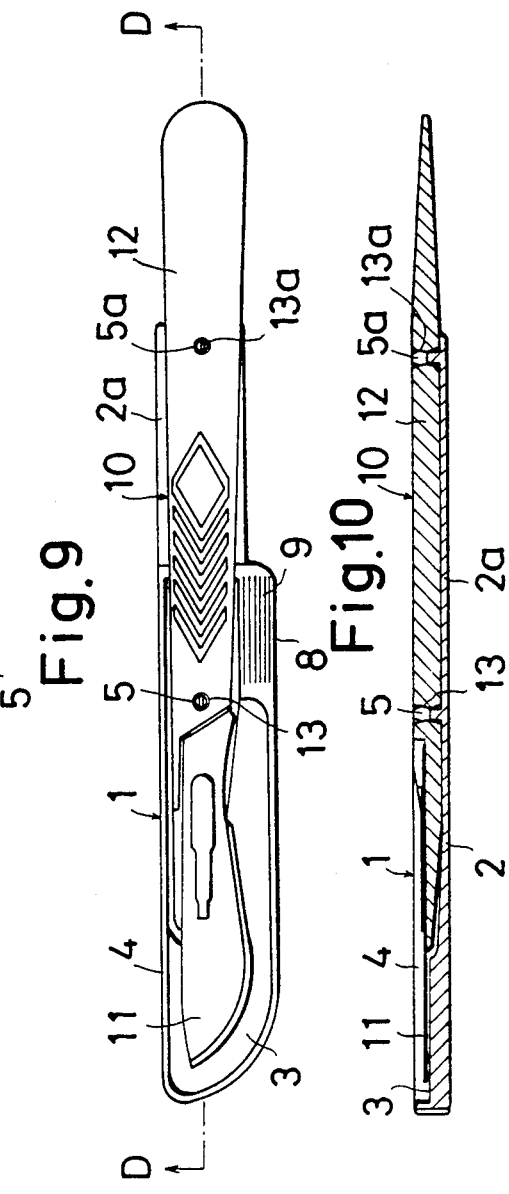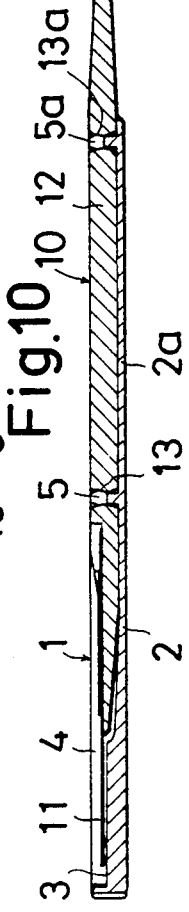

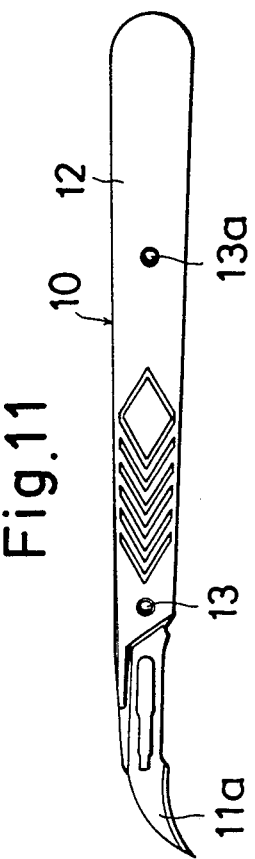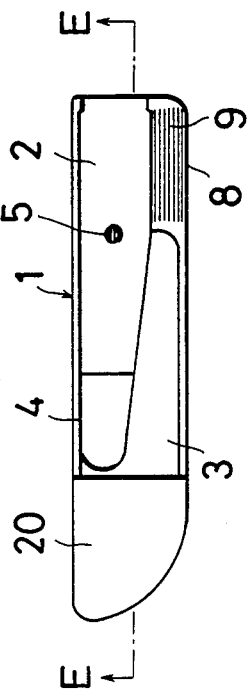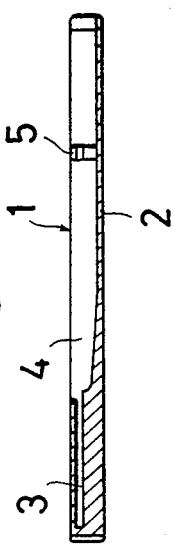

PROTECTOR FOR SURGICAL KNIFE

BACKGROUND OF THE INVENTION

Field of the Invention and Related Art Statements

The present invention relates to a protector for a surgical knife.

Nowadays, there has been widely used a surgical knife which is used only once. That is to say, a surgical knife is wasted after being used only once. The surgical knife has a particularly sharp edge and thus the surgical knife has to be handled very carefully. To this end, the surgical knife is inserted in a protector before and after the use, otherwise the edge of the knife might be damaged prior to the operation and fingers of the operator might be injured. The known surgical knife is inserted in a depression formed in an embossed plastic casing. In such a case, when a new knife is removed from the casing and the used knife is returned into the casing, the fingers might be injured. Further, the casing is complicated in construction and the cost of the casing is liable to be expensive.

SUMMARY OF THE INVENTION

The present invention has for its object to provide a novel and useful protector for a surgical knife which can avoid the above mentioned drawbacks of the known protector and an edge portion of the surgical knife can be easily inserted in the protector and a knife edge can be protected against the damage and user's fingers can be protected against the injury.

According to the invention a protector for a surgical knife having an edge portion and a step portion including at least one hole comprises a base plate having a peripheral shape substantially corresponding to that of the edge portion of the surgical knife;

a ridge portion formed along a periphery of the base plate except for a portion in which the stem portion of the surgical knife placed in the protector situates; and at least one projection formed on the base plate, said projection being inserted into said hole formed in the stem portion of the surgical knife.

BRIEF DESCRIPTION OF THE DRAWINGS

FIG. 1 is a plan view showing an embodiment of the protector according to the invention;

FIG. 2 is a side view of the protector shown in FIG. 1;

FIG. 3 is a cross sectional view cut along a line A—A in FIG. 1;

FIG. 4 is an enlarged side view illustrating a projection shown in FIG. 1;

FIG. 5 is a plan view showing the protector and a surgical knife inserted therein;

FIG. 6 is cross sectional view cut along a line B—B in FIG. 5;

FIG. 7 is a plan view depicting still another embodiment of the protector according to the invention;

FIG. 8 is a cross sectional view cut along a line C—C in FIG. 7;

FIG. 9 is a plan view showing the protector in which a knife is installed;

FIG. 10 is a cross sectional view cut along a line D—D in FIG. 9;

FIG. 11 is a plan view illustrating a surgical knife of another type;

FIG. 12 is plan view showing still another embodiment of the protector according to the invention; and FIG. 13 is a cross sectional view cut along a line E—E in FIG. 12.

DESCRIPTION OF THE PREFERRED EMBODIMENTS

FIG. 1 is a plan view showing an embodiment of the protector according to the invention, FIG. 2 is a side view thereof, and FIG. 3 is a cross sectional view cut along a line A—A in FIG. 1. The protector 1 comprises a base plate 2 having an edge receiving portion 3 which projects slightly from an upper surface of the remaining portion of the base plate and an upright ridge portion 4 formed along a periphery of the base plate 2 except for a portion through which a stem portion of a surgical knife extends outwardly. The protector 1 further comprises a projection 5 formed on the upper surface of the base plate 2 at a position at which a hole formed in the stem portion of the surgical knife is positioned when the surgical knife is placed on the protector 1. FIG. 4 shows the projection 5 in an enlarged scale. The projection 5 has a substantially cylindrical shape and comprises a top portion 6 which has a slightly larger diameter than that of the remaining portion. In the top portion 6 there is formed a slit 7 which extends in an elongated direction of the surgical knife placed on the protector 1. Therefore, the top portion 5 has a resiliency. The protector 1 further comprises a snap portion 8 having an anti-slip surface 9 formed thereon. The protector 1 is integrally formed by an injection mold of synthetic resin.

FIGS. 5 and 6 illustrate a condition in which the surgical knife is inserted in or placed on the protector 1. In case of placing a surgical knife 10 having edge portion 11, stem portion 12 and holes 13, 13a on the protector 1, the edge portion 11 is placed on the edge receiving portion 3 of the protector 1 and the projection 5 is inserted into the hole 13 formed in the stem portion 12 of the surgical knife 10. As illustrated in FIG. 6, the hole 13 has a tapered cross section and has the smallest diameter at its center. Therefore, after the top portion 6 of the projection 5 has been resiliently passed through the hole center, the projection 5 is firmly clamped in the hole 13. In this manner, the surgical knife 10 can be placed in the protector 1 very easily and positively and the knife is hardly removed out of the protector 1. In this installed condition, the edge portion 11 of the knife 10 is intimately placed on the edge receiving portion 3 of the protector 1 and thus the edge portion 11 does not protrude from the protector 1 so that the safety can be guaranteed.

In case of removing the surgical knife 10 out of the protector 1, the stem portion 12 of the knife is grasped with a right hand and the snap portion 8 is held with a left hand. Then the stem portion 12 is lifted and twisted. In this manner, the surgical knife 10 can be easily and safety removed from the protector 1. According to this embodiment, since the slit 7 formed in the top portion 6 of the projection 5 is aligned in the longitudinal direction of the protector 1, the resiliency of the projection 5 can be effectively used upon placing and nemoving the knife. Further, since a top end portion of the protector 1 is formed in accordance with an outer shape of the edge portion 11 of the knife 10, the user can recognize the direction of the edge of the knife easily from the shape of the protector.

FIGS. 7 and 8 show another embodiment of the protector according to the invention. The protector of the present embodiment comprises an extended base plate 2a integrally formed with the base plate 2. The extended base plate 2a extends in parallel with the atem portion 12 of the surgical knife 10 fit on the protector 1. On the surface of the extended base plate 2a is formed a second projection 5a similar to the first projection 5. As illustrated in FIGS. 9 and 10, the second projection 5a formed on the extended base plate 2a is resiliently inserted into the second hole 13a formed in the stem portion 12 of the surgical knife 10. In this manner, in the present embodiment, the surgical knife 10 is fixed firmly to the protector 1 at two positions.

It should be noted that the protector according to the present invention can be used not only for the surgical knives shown in FIGS. 5 and 9, but also for other surgical knives having various edge shapes. For instance, the protector can be used for a surgical knife 10 shown in FIG. 11.

FIGS. 12 and 13 depict still another embodiment of the protector according to the invention. In this embodiment, the protector 1 further comprises a lid-like plate 20 at a top end of the protector. Such a lid-like plate 20 can positively protect the edge portion 11 of the knife 10 and the operator can be further effectively protected from the edge portion of the knife.

As explained above in detail, the protector according to the invention utilizes the one or two holes inherently formed in the stem portion of the surgical knife and the knife can be positively and easily set in the protector by inserting one or two projections into one or two holes. In this manner, the knife edge can be effectively protected against the damage and at the same time, the user can be sufficiently protected from the sharp edge of the knife. Further, the protector according to the invention can be manufactured in a simple and cheap manner.

What is claimed is:

1. A protector for a surgical knife having an edge portion and a stem portion including at least one hole comprising a base plate having a peripheral shape substantially corresponding to that of the edge portion of the surgical knife;

a ridge portion formed along a periphery of the base plate except for the portion of the periphery of the base plate in which the stem portion of the surgical knife situates when said surgical knife is placed in the protector; and at least one projection formed on and projecting from the base plate, said projection being adapted to be inserted into a hole formed in the stem portion of the surgical knife.

2. A protector according to claim 1, wherein said base plate, a ridge portion and projection are integrally formed of synthetic resin.

3. A protector according to claim 2, wherein said base plate further comprises an edge receiving portion which projects slightly from a remaining portion of the base plate.

4. A protector according to claim 1, wherein a top portion of said projection has a slit formed therein so that said top portion may resiliently engage said hole formed in said stem portion.

5. A protector according to claim 4, wherein said slit is aligned with the longitudinal axis of the surgical knife.

6. A protector according to claim 1, further comprising a snap portion having an anti-slip surface, said snap portion being formed at a rear portion of the protector.

7. A protector according to claim 1, further comprising a base plate extension integrally formed with and extending from the base plate, said base plate extension extending in parallel with and coincidental to the stem portion of the surgical knife.

8. A protector according to claim 7, further comprising a second projection formed on said base plate extension, said second projection being adapted to be inserted into a second hole formed in the stem portion of the surgical knife.

9. A protector according to claim 1, further comprising a lid-like plate formed at a front end portion of the base plate which together with said base plate defines a cavity adapted to receive said edge portion of said surgical knife.

* * * * *